United States Patent

Remsburg

[11] Patent Number: 5,959,535
[45] Date of Patent: Sep. 28, 1999

[54] ELECTROGALVANIC-POWERED DIAPER WETNESS SENSOR

[76] Inventor: Ralph Remsburg, 27 Morena, Austin, Tex. 92715

[21] Appl. No.: 08/948,236

[22] Filed: Oct. 9, 1997

Related U.S. Application Data

[63] Continuation of application No. 08/575,514, Dec. 20, 1995, abandoned.

[51] Int. Cl.[6] ..................................................... G08B 21/00
[52] U.S. Cl. .......................... 340/604; 340/573; 340/603; 128/886
[58] Field of Search ................................ 340/384.1, 573, 340/603, 586, 604, 605

[56] References Cited

U.S. PATENT DOCUMENTS

| | | | |
|---|---|---|---|
| 2,127,538 | 8/1938 | Seiger | 128/138 |
| 3,199,095 | 8/1965 | Ashida | 128/886 |
| 3,245,068 | 4/1966 | Wegryn et al. | 340/235 |
| 3,508,235 | 4/1970 | Baisden | 340/573 |
| 3,530,855 | 9/1970 | Baldino | 128/138 |
| 3,696,357 | 10/1972 | Kilgore | 340/235 |
| 3,759,246 | 9/1973 | Flack et al. | 128/2 R |
| 4,069,817 | 1/1978 | Fenole et al. | 128/138 A |
| 4,539,559 | 9/1985 | Kelly et al. | 340/573 |
| 4,851,816 | 7/1989 | Macias et al. | 340/573 |
| 5,101,657 | 4/1992 | Lahlouh et al. | 340/604 |
| 5,266,928 | 11/1993 | Johnson | 340/604 |
| 5,392,032 | 2/1995 | Kline et al. | 340/604 |
| 5,570,082 | 10/1996 | Mahgerefteh et al. | 340/604 |

Primary Examiner—Michael Horabik
Assistant Examiner—Timothy Edwards, Jr.
Attorney, Agent, or Firm—Klima & Pezzlo, P.C.

[57] ABSTRACT

An electrical wetness sensor powered by the electrogalvanic action of an anode, a cathode and an electrolyte. In the preferred embodiment the electrolyte is urine and the device is used to warn of incontinence. This device contains the following features: sensitivity to wetness; electrical battery-less operation; hermetic and permanent sealing; no-maintenance operation; portability, inexpensiveness, and disposableness. The alarm unit may be configured to produce a visual and/or audible signal. In the preferred embodiment the alarm unit transmits a signal to a remote FM radio receiver or dedicated device to announce incontinence. Incontinence is announced by a tone, visual signal, silencing of the radio station the receiver is tuned to, or activation of a microphone within the alarm unit to allow remote listening. Any or all of these indications may be designed into the device and are discussed.

16 Claims, 5 Drawing Sheets

ELECTROGALVANIC-POWERED DIAPER WETNESS SENSOR

This application is a continuation of prior U.S. appl. Ser. No. 08/575,514, filed Dec. 20, 1995, now abandoned.

BACKGROUND—FIELD OF INVENTION

The present invention relates to a device which indicates wetness. Specifically to devices which indicate wetness using a disposable wetness sensor providing power to an alarm, the alarm unit powered by electrogalvanic action within the liquid.

BACKGROUND—DESCRIPTION OF PRIOR ART

Bladder incontinence is endemic in the very young. The young are generally trained during the second and third year to avoid incontinence. Until the problem of incontinence is resolved, diapers are normally worn by the infant in training.

Incontinence is also a problem among the aged, and the infirmed of any age. Loss of bladder control in these individuals is usually due to physiological, neurological, or psychological disorders. Often there is no warning that the undergarments are becoming wet until the wetness causes discomfort or is noticed by others, causing embarrassment.

Urine is a solution of chemicals and is an electrolyte which will therefore conduct an electrical current. Healthy kidneys produce urine with pH ranging widely from 4.5 to 8.0, but the pooled daily specimen is usually acid (pH 6). Decreased pulmonary ventilation during sleep produces respiratory acidoses and a highly acid urine. After a meal the urine becomes less acid (alkaline tide) and a few hours later more acid. A diet rich in animal protein, typical of the western hemisphere, results in an acid urine, while a predominantly vegetable diet results in an alkaline urine. A hot, dry climate will often yield a highly concentrated, acid urine which may be irritating when passed.

Various proposals have been made in the signaling of urinary incontinence. For example, diaper-like garments have been constructed to render the results of incontinence less inconvenient, and mechanical devices have been worn (externally or internally) whereby incontinence may be controlled. Implantable devices have been constructed to enhance muscle control, and electrical devices are made to provide an electrical shock upon incontinence.

Many wetness-sensing devices are known to those skilled in the art. Most warning devices use electrodes within the undergarment. A battery supplies electricity which is passed through these electrodes to determine if incontinence has occurred. Such devices have been rejected in the marketplace by consumers due to the concern of battery-powered electrodes in contact with an infants genitals. There is a great need for a device which does not require a battery to sense and warn of incontinence.

An arrangement disclosed by Flack et al., in U.S. Pat. No. 3,759,246 contains a quilt-like undergarment into which electrodes are woven. Electricity is continually passed through the electrodes while electrical resistance is measured. The electrical resistance changes greatly when an electrolyte forms an electrical path within the undergarment, thereby indicating urinary incontinence. Because electrical resistance is greatly affected by minute variations in the salt content of the urine, Flack et al., suggest pre-loading the garment with a 5 percent by weight aqueous sodium chloride solution to provide a baseline datum level. This indicates that the circuit is always complete and electrical current is always present in the undergarment. In addition, this device is made expensive by salt pre-loading and is sensitive to small amounts of salt-containing perspiration. There is a great need for a device to sense incontinence that is portable, inexpensive, and disposable.

In U.S. Pat. No. 4,539,559 to Kelly et al., describe a device which comprises a portable, disposable sensor unit for urinary incontinence. Again, as in other devices, a battery is required to produce the electromotive force when an electrolyte such as urine completes the circuit. The inventors realized the negative consumer reaction to an electrical battery within the unit and devised a complex fail-safe circuit which reduces the perceived hazard to an electromotive force of 9 volts and an electrical current of 10 microamperes. This device then requires a portable battery enclosure which is unaffected by fluid leakage, yet can be disassembled to allow battery replacement. There is a great need for a device which does not require the periodic maintenance of battery replacement.

U.S. Pat. Nos. 2,127,538 to Seiger, 4,069,817 to Fenole et al., and 3,530,855 to Balding are other examples of battery powered open electrode circuits for detecting incontinence. Variation to the basic incontinence sensor are taught in U.S. Pat. No. 3,696,357 to Kilgore, and U.S. Pat. No. 3,245,068 to Wegryn, et al. The former discreetly signals incontinence to the user by means of an audible signal located in a headband. The latter has means to calibrate the sensor to liquid volume by use of a thyatron and conductive inks painted on the sensing garment.

All such battery-operated devices must contain a protruding positive and a negative voltage terminal. An inherent danger in all such battery-operated devices is that the unit may become separated from the sensor unit within the infant's immediate area. The unit may then be brought to the infant's mouth whereby an electrical shock may occur from the battery contained within the unit. Perhaps a greater danger may be that since such devices must have a provision for disassembly for battery replacement, the unit may be disassembled by the infant and the smaller pieces may then be ingested by the infant. There is a great need for a device which does not require the periodic maintenance of battery replacement and is therefore hermetically and permanently sealed.

Still, there is a great need for a device containing the following features: sensitivity to wetness; electrical battery-less operation; hermetic and permanent sealing; no-maintenance operation; portability, inexpensiveness, and disposableness.

OBJECTS AND ADVANTAGES

I have found a device which solves the problems listed above in a unique way, comprising a disposable sensor unit and a portable alarm unit. These units are described and characterized more fully in the following discussion.

This invention relates to a portable electronic device for producing a signal whereby an audio and/or visual alarm is observed when an undergarment is wetted by urine. More specifically it relates to a device which indicates wetness by means comprising a disposable wetness sensor providing power to an alarm, said power generated by an electrogalvanic action within the urine.

Therefore in accordance with an aspect of the present invention, several primary objects and advantages of the present invention are:

(a) to provide a new and improved method and apparatus to detect urine-wetted undergarments;

(b) to provide a new method and apparatus for detecting urine-wetted undergarments whereby no electrical battery is required;

(c) to provide a new method and apparatus for detecting urine-wetted undergarments whereby no electrical battery is required and therefore no periodic maintenance is required;

(d) to provide a new method and apparatus for detecting urine-wetted undergarments whereby no electrical battery is required and therefore the alarm unit may be hermetically sealed;

(e) to provide a new and improved apparatus for detecting urine-wetted undergarments whereby the unit is self-contained and thereby portable;

(f) to provide an improved method and apparatus for detecting urine-wetted undergarments whereby the sensor unit is disposable;

(g) to provide an improved method and apparatus for detecting urine-wetted undergarments whereby the assembled unit is comparatively inexpensive to other such devices based upon battery operation;

(h) to provide a new method and apparatus for detecting urine-wetted undergarments whereby the alarm unit is passive and cannot harm the infant, even during oral use by the infant;

(i) to provide an alarm unit of the wetness sensor described above that transmits an alarm signal and therefore does not disturb the infant upon activation by incontinence.

These and other objects and advantages of the present invention will no doubt become obvious to those of ordinary skill in the art after having read the following detailed description of the preferred embodiment, which is illustrated in the various drawing figures.

DRAWING FIGURES

The invention can be more fully understood in relation to the accompanying drawings which show in detail a preferred embodiment.

| Reference Numerals in Drawings | | | |
|---|---|---|---|
| 10 | alarm unit | Q1 | transistor |
| 11 | alarm component | Q2 | transistor |
| 12 | hermetically sealed enclosure | Q3 | transistor |
| 13 | alarm unit V+ connector | L1 | tuning coil |
| 14 | alarm unit V− connector | LED | light emitting diode |
| 19 | piezo element | ANT | antenna |
| 20 | disposable sensor unit | ECM | electret condenser microphone |
| 21 | anode element | | |
| 22 | dielectric liner | | |
| 23 | cathode element | | |

-continued

| Reference Numerals in Drawings | |
|---|---|
| 24 | adhesive strip |
| 25 | sensor unit V+ connector |
| 26 | sensor unit V− connector |
| 27 | sensor probe |
| 30 | diaper |
| R1 | resistor |
| R2 | resistor |
| R3 | resistor |
| R4 | resistor |
| R5 | resistor |
| R6 | resistor |
| R7 | resistor |
| R8 | resistor |
| R9 | resistor |
| C1 | electrolytic capacitor |
| C2 | capacitor |
| C3 | capacitor |
| C4 | capacitor |
| C5 | capacitor |
| C6 | capacitor |
| C7 | electrolytic capacitor |

DESCRIPTION OF THE PREFERRED EMBODIMENT

FIGS. 1 to 5

Figure 1:
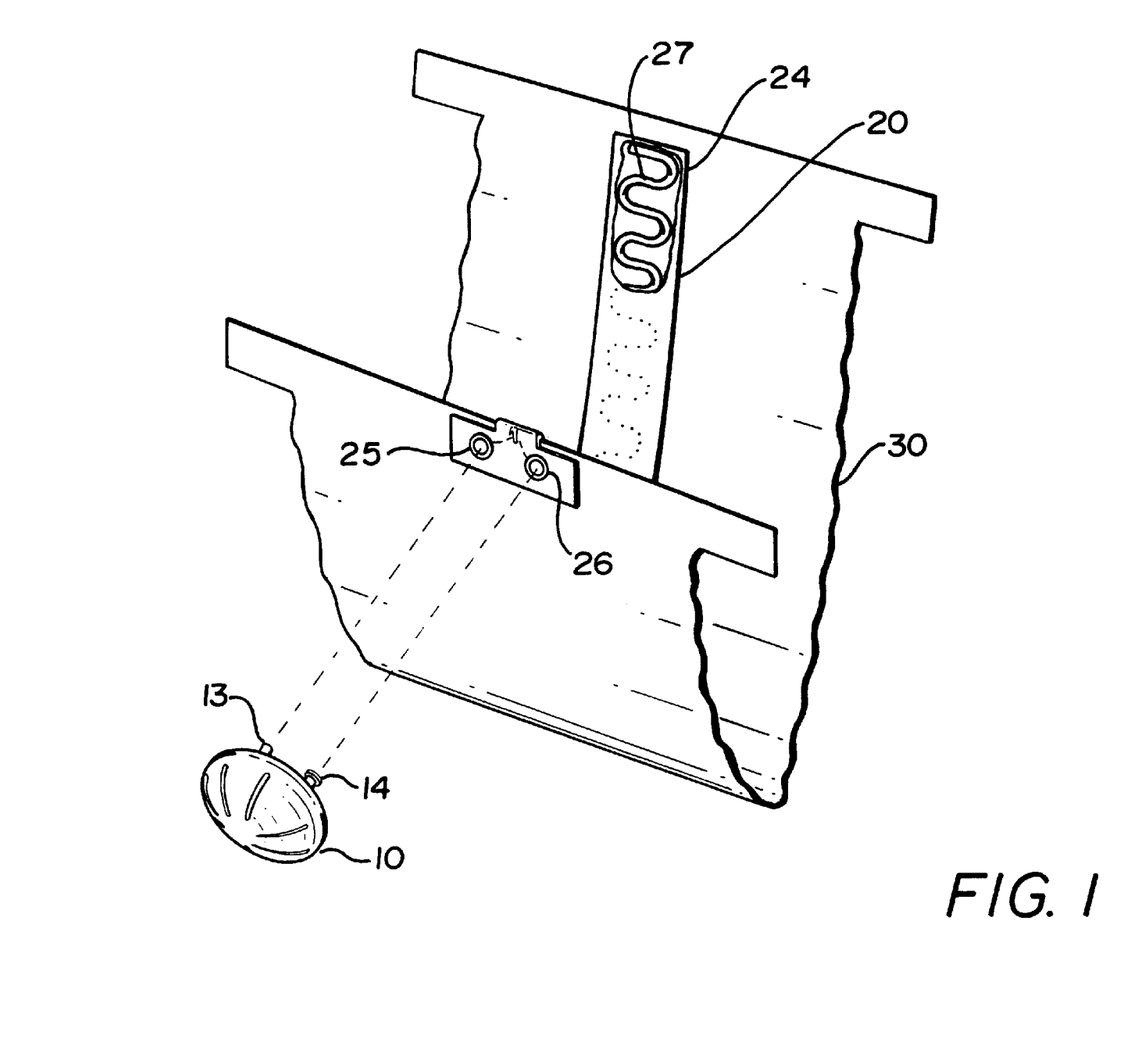
FIG. 1 shows an isometric overall view of the assembled sensor and diaper, demonstrating the unconnected alarm unit.

FIG. 1 illustrates an external isometric overall view of the electrogalvanic-powered diaper wetness sensor, which is comprised of two primary units, an alarm unit 10 and a disposable sensor unit 20 both of which may be mounted to a diaper 30.

Alarm unit 10 as shown is generally preferred to be small so as to not cause discomfort if the infant should happen to lay upon it. Alarm unit 10 should also be large enough that the infant can not swallow it should the unit become separated from diaper 30/disposable sensor 20 assembly. Generally, the preferred shape of alarm unit 10 is a disc with rounded contours approximately 50 mm in diameter.

Figure 3A:
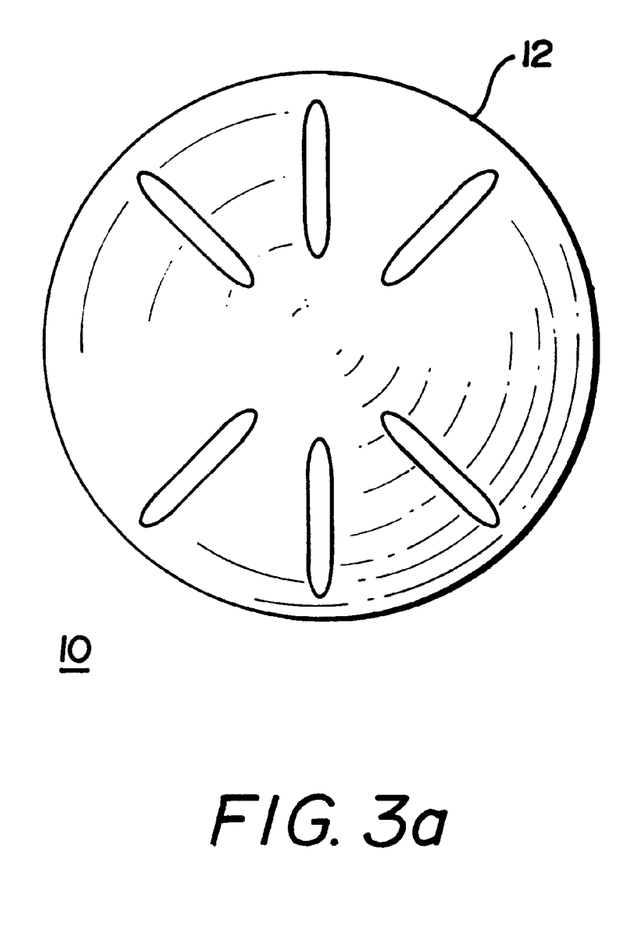
FIG. 3a illustrates the sealed alarm unit in a top view.
Figure 3B:
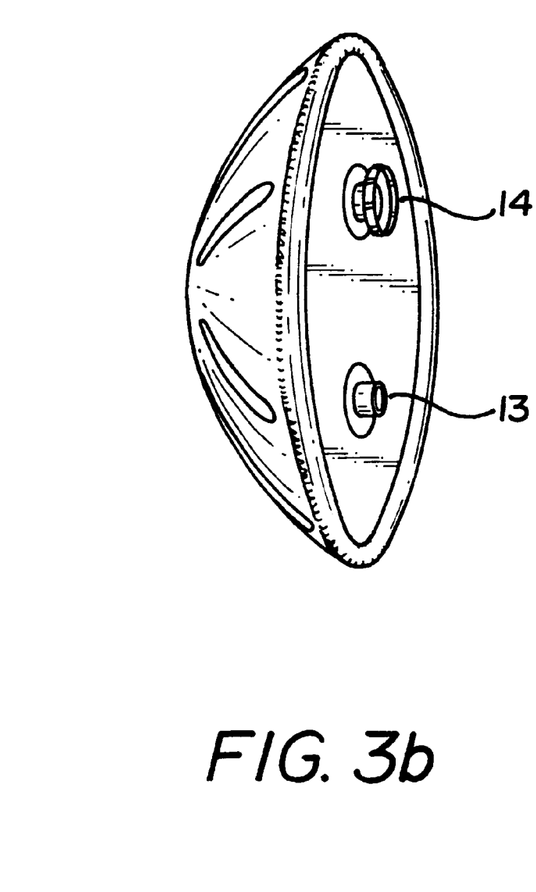
FIG. 3b depicts the alarm unit in a side view.

Referring now to FIG. 3a a hermetically sealed housing 12 of alarm unit 10 can be seen more clearly. The housing is recommended to be constructed of a material known to be unaffected by prolonged exposure to urine and of a non-toxic grade of polymer such as acrylic, or a non-toxic grade of elastomer such as silicone. The exact shape, size, and material of hermetically sealed housing 12 of alarm unit 10 may provide other advantages as a resonant sounding surface in some embodiments. Referring now to FIG. 3b an alarm unit V+ connector 13 and an alarm unit V− connector 14 are seen to protrude from alarm unit 10.

Referring again to FIG. 1 connectors 13 and 14 are seen and should ideally provide simultaneous mechanical and electrical connection to disposable sensor unit 20. There are many known methods of providing such mechanical and electrical connection, and the preferred embodiment contains snap connectors similar to those seen on a standard 9 volt battery (NEDA #1604), but spaced farther apart. Connectors 13 and 14 should be constructed of an electrically conductive material which will not react during prolonged exposure to urine. Although there are many materials known to be compatible with urine, a grade of stainless steel containing approximately 18 percent chromium and 8 percent nickel is used in the preferred embodiment.

Disposable sensor unit 20 comprises an adhesive strip 24, a sensor probe 27, a sensor unit V+ connector 25, and a sensor unit V− connector 26. In the preferred embodiment, adhesive strip 24 is constructed of a low-cost, absorbent, bio-degradable material such as paper fiber approximately 45 cm long and approximately 10 cm wide. In the preferred embodiment adhesive strip 20 has one side coated with an adhesive which is protected by a removable non-stick material. Sensor probe 27 is attached to the adhesive side of adhesive strip 24 in a serpentine shape. At one end of adhesive strip 24 are placed sensor unit V+ connector 25, and sensor unit V− connector 26. These snap connectors are the mechanical opposite of alarm unit V+ connector 13, and alarm unit V− connector 14 respectively, and therefore provide a physical and electrical connection between alarm unit 10 and disposable sensor unit 20 when connected by pressing together.

Figure 2:
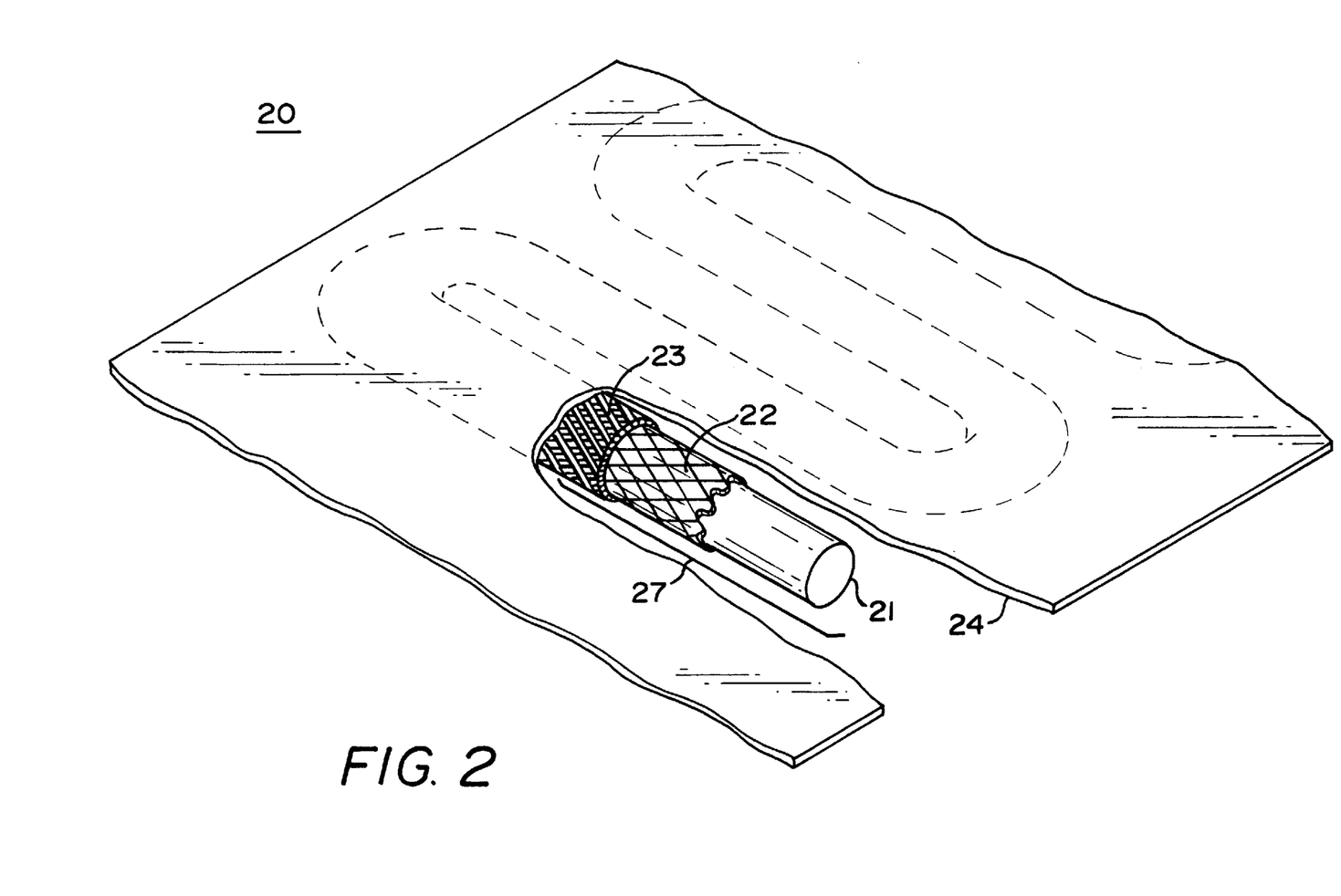
FIG. 2 is a cut-away drawing of the disposable senor unit.

Referring now to FIG. 2, a close-up view of disposable sensor unit 20 is seen. Sensor probe 27 comprises an anode element 21, a dielectric liner 22, and a cathode element 23. The material of anode element 21 is an electrically conductive wire or rod that is anodic in relation to the material chosen for cathode element 23. These materials are not required to be unaffected by urine, since the whole of sensor unit 20 is disposable after one use. The materials should be non-toxic and non-irritating to sensitive human skin. There are many materials that will satisfy the anodic/cathodic relationship. The preferred embodiment comprises an AZ 31B magnesium anode element 21 and an AM 350 grade stainless steel cathode element 23.

The preferred material composition of magnesium anode element 21 is as follows: 2.5% to 3.5% Aluminum, 0.20% minimum Manganese, 0.60% to 1.4% Zinc, 0.04% maximum Calcium, 0.10% maximum Silicon, 0.05% maximum Copper, 0.005% maximum Nickel, 0.005% maximum Iron, 0.30% maximum other impurities, with the remaining material percentage being Magnesium.

The preferred material composition of stainless steel cathode element 23 is as follows: 16.0% to 17.0% Chromium, 4.0% to 5.0% Nickel, 2.5% to 3.25% Molybdenum, 0.50% to 1.25% Manganese, 0.50% maximum Silicon, 0.07% to 0.13% Nitrogen, 0.07% to 0.11% Carbon, 0.04% maximum Phosphorous, 0.03% Sulfur, with the remaining material percentage being Iron.

The preferred treatment of magnesium anode element 21 is a chrome pickle treatment. Such pickling baths are well known in the art and may be achieved by processing magnesium in a seven stage process as follows:

| Solution | Constituent | Concentration (grams/Liter) | Temperature (° C.) | Cycle Time (Minutes) |
| --- | --- | --- | --- | --- |
| Cleaner | Na$_4$P$_2$O$_7$ | 30 g/L | | |
| | Na$_2$B$_4$O$_7$:10H$_2$O | 68 g/L | | |
| | NaF | 8 g/L | | |
| | Deionized Water | Remaining | 77 to 82° C. | 2 to 5 |
| Cold Rinse | Deionized Water | — | Ambient | 0.25 |
| Acid Pickle | 100% HF | 143 to 196 g/L | | |
| | H$_2$SO$_4$ | 48 g/L | | |
| | Deionized Water | Remaining | 21 to 32° C. | 2 to 5 |
| Cold Rinse | Deionized Water | — | Ambient | 0.25 |
| Chrome Pickle | NaHF$_2$ | 15 g/L | | |
| | NaCr$_2$O$_7$:2H$_2$O | 180 g/L | | |
| | Al$_2$(SO$_4$):14H$_2$O | 10 g/L | | |
| | HNO$_3$ (sp. gr. 1.42) | 120 g/L | | |
| | Deionized Water | Remaining | 21 to 32° C. | 0.5 |
| Cold Rinse | Deionized Water | — | Ambient | 0.25 |
| Hot Rinse | Deionized Water | — | 71 to 82° C. | 0.5 |

The preferred treatment of stainless steel cathode element 23 is a passivation treatment. Such passivation baths are well known in the art and may be achieved by processing stainless steel in a four stage process in the following manner:

| Solution | Constituent | Concentration | Temperature (° C.) | Cycle Time (Minutes) |
| --- | --- | --- | --- | --- |
| Passivation | 70% HNO$_3$ | 30 to 90 g/L | 82 to 95° C. | 30 |
| | Na$_2$Cr$_2$O:2H$_2$O | 4% to 6% | | |
| | Deionized Water | Remaining | Ambient | 30 |
| Cold Rinse | Deionized Water | — | Ambient | 0.25 |
| Hot Rinse | Deionized Water | — | 71 to 82° C. | 0.5 |

Many other materials may be used to achieve an anodic/cathodic relationship in a urine solution. For example, precious metals such as Silver, Palladium, and Gold are known in the art to be highly cathodic. These metals may be substituted for the preferred AM 350 stainless steel but may increase the cost of sensor probe 27 by an unacceptable margin. Although the surface of anode element 21 and cathode element 23 should be constructed of materials displaying an anodic/cathodic relationship, the entire element is not required to be constructed of materials displaying the preferred electrogalvanic reaction. For example, anode element 21 may be constructed of a nylon fiber plated with a thin layer of magnesium. Dielectric line 22 may be constructed of a material of absorbent cotton having an outer plating of stainless steel applied by the process of chemical vapor deposition.

An additional relationship between anode element 21 and cathode element 23 is that cathode element 23 should have several times the surface area of anodic element 21. One method to achieve this relationship in a small and flexible envelope is shown in FIG. 2 whereby cathode element 23 is a braided wire in a coaxial relationship to anode element 21. Dielectric liner 22 electrically separates anode element 21 and cathode element 23. Dielectric liner 22 should be constructed of a material displaying strong absorbent and hydrophilic properties in order to retain the urine to propagate the galvanic reaction. Sensor probe 27 is attached to the adhesive side of adhesive strip 24. Many arrangements of sensor probe 27 on adhesive strip 24 are possible. The preferred embodiment is a serpentine sensor probe 27. Many sizes of sensor probe 27 are also possible. The preferred embodiment comprises a 36 gauge (0.13 mm) anode element 21, a 0.30 mm thick dielectric liner 22, and a braided 36 gauge (0.13 mm) 16-wire cathode element 23.

Figure 4:
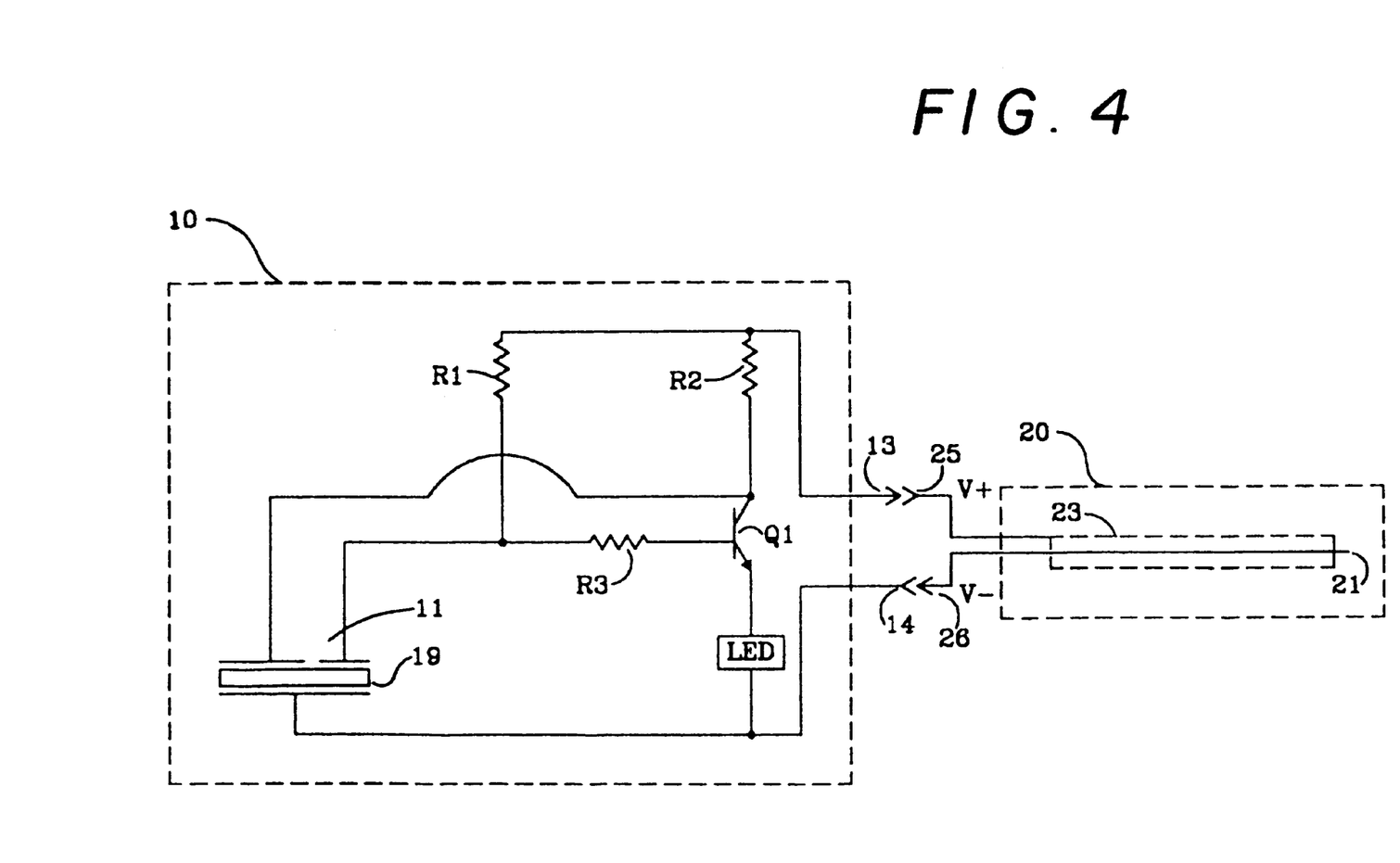
FIG. 4 presents an electronic schematic wiring diagram of a possible embodiment of the entire disposable sensor/alarm unit.

Referring now to FIG. 4, an electrical wiring schematic of one embodiment of the present invention is shown. Within the sealed enclosure of alarm unit 10 are a resistor R1, a resistor R2, and a resistor R3. Also within alarm unit 10 are an NPN transistor Q1, a light emitting diode LED, and an alarm component 11, which in the preferred embodiment is a piezo element 19. Physical and electrical connection to disposable senor unit 20 are made by alarm unit V+ connector 13 and alarm unit V− connector 14.

The resistors can be any type of resistive element. Typically R1 has a value of 220KΩ and R2 has a value of 470Ω. NPN transistor Q1 should be of a design capable for use in general purpose amplifying applications such as a type MPS2222A. Piezo element 19 of alarm component 11 is of the type requiring a low level voltage and current to produce an audible output signal.

Disposable sensor unit 20 is comprised of anode element 21, cathode element 23, a sensor unit V+ connector 25, and a sensor unit V− connector 26. Sensor unit V+ connector 25 and sensor unit V− connector 26 are designed to be mateable with alarm unit V+ connector 13 and alarm unit V− connector 14 respectively.

Figure 5:
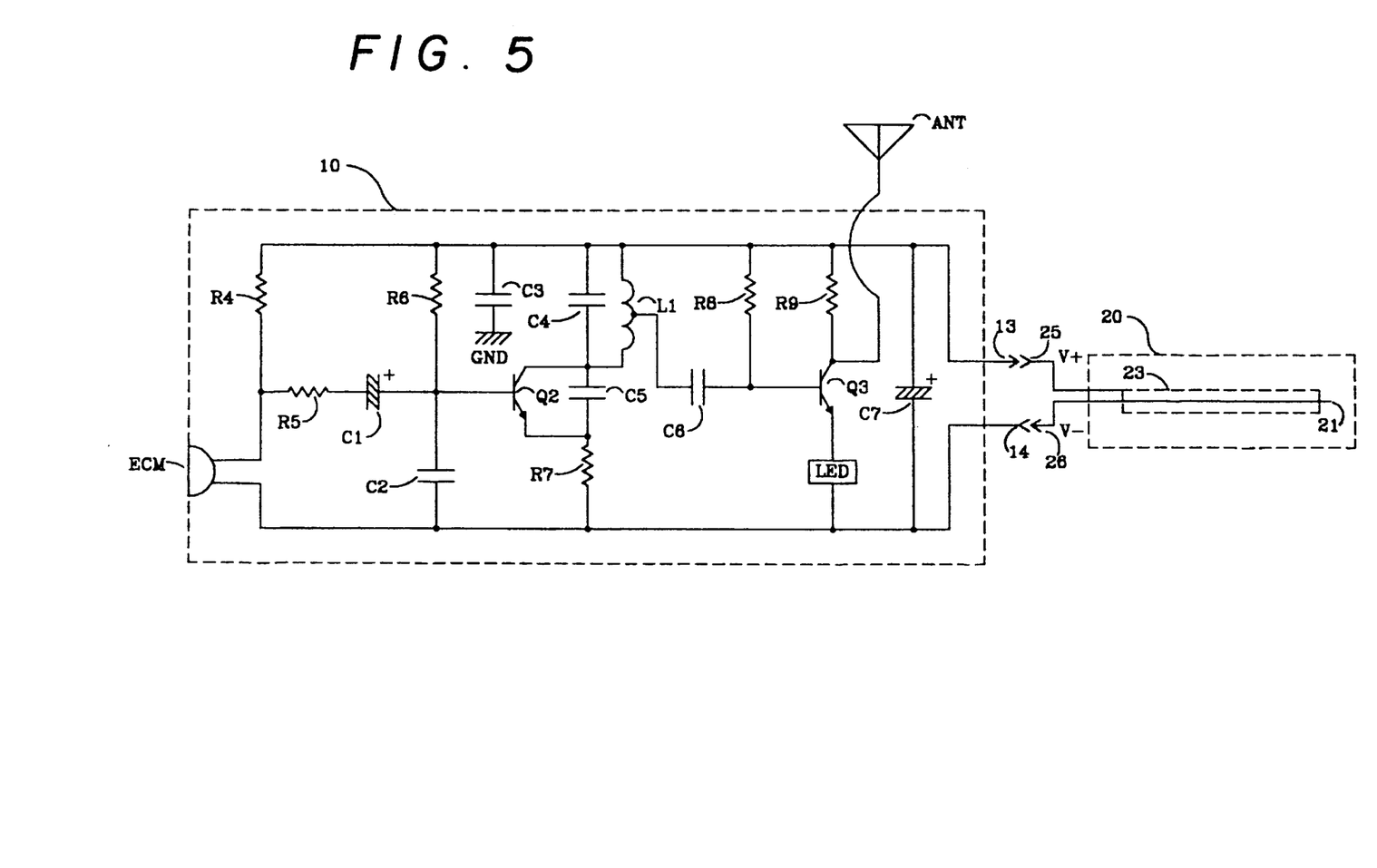
FIG. 5 presents an electronic schematic wiring diagram of a preferred embodiment of the entire disposable sensor/alarm unit with integral transmitter.

An electrical schematic of the preferred embodiment of the present invention is shown in FIG. 5. Within alarm unit 10 are six resistors labeled R4 through R9, two electrolytic capacitors C1 and C7, five capacitors labeled C2 through C6, two NPN transistors labeled Q2 and Q3, a tuning coil labeled L1, an electret condenser microphone labeled ECM, and an antenna labeled ANT which is also contained within hermetically sealed enclosure 12 of alarm unit 10. The other items shown in FIG. 5 are identical to those items described for use in the embodiment shown in FIG. 4.

The circuit shown in FIG. 5 is a simple wireless transmitter. The following values may be used for the components:

| | |
|---|---|
| R4 | 1.2KΩ resistor |
| R5 | 10KΩ resistor |
| R6, R8 | 33KΩ resistor |
| R7 | 100Ω resistor |
| R9 | 180Ω resistor |
| C1, C7 | 10 μF electrolytic capacitor |
| C2 | 100 pF capacitor |
| C3 | 0.01 μF capacitor |
| C4, C6 | 4 pF capacitor |
| C5 | 10 pF capacitor |
| Q2, Q3 | NPN transistor type 2SC1923 |
| L1 | 0.27 μH to 0.30 μH tuning coil |
| ANT | antenna wire approximately 0.8 m long. |

There are a great number of variations that are possible to the basic electrical circuits depicted in FIG. 4 and FIG. 5. For example, piezo element 19 may be attached to hermetically sealed enclosure 12 to produce a more audible sound through resonance; preferred piezo element 19 may be replaced by a miniature buzzer; electret condenser microphone ECM may be replaced by an additional oscillator circuit to produce an audible tone on a typical FM radio receiver tuned to the frequency of alarm unit 10; electret condenser microphone ECM may be eliminated entirely in which case an FM radio receiver will produce silence at the frequency that alarm unit 10 is tuned to, when alarm unit 10 is activated; light emitting diode LED may be eliminated or replaced by another visual indicator such as a Liquid Crystal Diode; etc.

OPERATION

FIGS. 1 to 5

Referring to FIG. 1, disposable sensor unit 20 is attached to diaper 30. Said attachment may be by means of adhesive strip 24, shown more clearly in FIG. 2, which covers one side of disposable sensor unit 20. In a convenient manner, a portion of disposable sensor unit 20 may be folded over diaper 30 so that sensor unit V+ connector 25 and sensor unit V− connector 26 are on the outer surface of diaper 30. Alarm unit 10 may then be attached to disposable sensor unit 20 by means of interlocking snaps shown as alarm unit V+ connector 13 and alarm unit V− connector 14. Alarm unit V+ connector 13 and alarm unit V− connector 14 are seen more clearly in FIG. 3a and 3b. Alarm unit 10 is encased in hermetically sealed enclosure 12. Referring again to FIG. 1, said snaps provide electrical and mechanical connection to corresponding snaps shown as sensor unit V+ connector 25 and sensor unit V− connector 26 on the outer surface of diaper 30 in FIG. 1.

Referring now to FIG. 2, disposable sensor unit 20 contains sensor probe 27. Upon incontinence, urine will seep through the upper surface of disposable sensor unit 20 and will initially contact cathode element 23. Driven by gravity and the capillary action of the braided wires of cathode element 23, urine will spread and be drawn into contact with dielectric liner 22. Dielectric liner 22 also exhibits a capillary action which spreads and draws the urine into contact with anode element 21.

When urine is in contact with both cathode element 23 and anode element 21 an electrogalvanic cell is activated. The electrochemical nature of the electrogalvanic cell is more fully described in the following section entitled Theory of Operation. An electromotive force is then seen to form across cathode element 23 and anode element 21. Dielectric liner 22 maintains the electrogalvanic cell by retaining urine which is in contact with both cathode element 23 and anode element 21.

Referring now to FIG. 4, an electrical schematic of a possible embodiment of the present invention is shown. This circuit is well known to those skilled in the art and is commonly used to produce an audible and/or visual signal upon activation. Voltage is generated in the electrogalvanic cell by the electrochemical action of disposable sensor unit 20, comprised of cathode element 23 and anode element 21. Voltage is transmitted from sensor unit V+ connector 25 to alarm unit V+ connector 13, and from sensor unit V− connector 26 to alarm unit V− connector 14. The voltage is used to activate light emitting diode LED and alarm component 11. Alarm component 11 may be any number of audible warning devices and in this embodiment is piezo element 19. Resistors R1, R2, and R3 provide the necessary resistance for proper operation of the circuit. When the electrical voltage provided by the electrogalvanic cell flows to alarm unit 10, it is applied to the base of transistor Q1. The application of voltage activates transistor Q1 whereby voltage is applied across light emitting diode LED and piezo element 19. Producing both an audible and/or visual signal of incontinence.

Although the circuit of FIG. 4 is simple and well known solution to the problem of a low-cost alarm unit, there are several disadvantages with the design. Primary among these is that the infant may associate the audible tone of piezo element 19 with incontinence, causing some psychological trauma.

Referring now to FIG. 5, an electrical schematic of a preferred embodiment of the present invention is shown. The electrical schematic of FIG. 5 represents a Frequency Modulated transmitter suitable for use in the frequency range of 91 to 97 MHZ. Such devices are well known to those skilled in the art. This device will transmit an FM band radio signal to a maximum distance of approximately 10 meters.

In the preferred embodiment of FIG. 5, the frequency of the radiated signal is controlled by the output of electret condenser microphone ECM. Basic operation of the circuit is as follows: Voltage is generated in the electrogalvanic cell by the electrochemical action of disposable sensor unit 20, comprised of cathode element 23 and anode element 21. Voltage is transmitted from sensor unit V+ connector 25 to alarm unit V+ connector 13, and from sensor unit V– connector 26 to alarm unit V– connector 14. Upon activation of the circuit by the presence of urine in disposable sensor unit 20, electret condenser microphone ECM causes the oscillating frequency of transistor Q2 to vary in proportion to the signal provided by electret condenser microphone ECM. Greater signal produce a greater frequency variance. The signal for Q2 is transmitted to transistor Q3 which acts as an amplifier. The signal is then delivered from transistor Q3 to antenna ANT whereby the signal is radiated. The frequency of the signal is controlled by tuning coil L1. The application of voltage to transistor Q3 also applies voltage across light emitting diode LED, signaling incontinence to those within the immediate area of the infant. Resistors R4 through R9 provide the necessary resistance required by the circuit. Capacitors C1 through C7 provide the necessary circuit capacitance.

The radiated output of alarm unit 10 may then be received by a standard FM band radio receiver. If the receiver is tuned to the same frequency as tuning coil L1, the audible sound received by electret condenser microphone ECM may be heard. If the FM band radio receiver is tuned to an existing radio station and is within the maximum useable range of approximately 5 meters distance from alarm unit 10 the radio station will be silenced by alarm unit 10, allowing the audible signal of electret condenser microphone ECM to be heard. If no sound is present for electret condenser microphone ECM to deliver via alarm unit 10, then the existing radio station signal will be silenced. If desired, a dedicated FM band receiver may be used in place of a standard FM band radio receiver. An oscillator circuit may be used in place of electret condenser microphone ECM to produce an alarm tone in the FM band receiver. Many other variation to this basic design will be noticed to those skilled in the art.

After incontinence, disposable sensor unit 20 may be discarded along with diaper 30. Alarm unit 10 may be reused.

THEORY OF OPERATION

Normal corrosion, termed "local cell corrosion", of a metal in an electrolyte such as urine involves the flow of current from the local anodic site to a local cathodic site on the surface of the metal. Relatively small differences in the voltage potentials of local cells are the result of slight compositional, ionic concentration, or differential aeration dissimilarities on the metal surface. These are caused by variances in, metal phase, crystal orientation, grain boundaries, etc. The more inhomogeneous the surface is, the more susceptible it is to local cell corrosion. Dissolution of the anode relates to the galvanic current according to Faraday's law:

$$W = Ite/Q_F$$

Where:

W=weight or quantity of metal dissolved,

I=electrical current, t=time duration of current flow, e=equivalent of the anode material (atomic weight divided by the valance or charge of ions produced), $Q_F$=Faraday unit.

Galvanic corrosion occurs when dissimilar metals are placed in near contact, or otherwise connected electrically through an electrolyte, and generate an electric current. The corrosion is accelerated for the active metal and decreased in the less active, or cathodic, metal. The basic factors in this type of corrosion are the electrical potentials of the metals, current, and resistances.

The polarization of the metals in an electrolyte solution usually occurs because of a film of oxide on the metal surface. This change reduces the voltage potential difference relative to the open circuit potential voltage, and causes the corrosion rate to decrease. The decrease in corrosion rate increases the ionic resistance of the external circuit and diminishes the current flow.

Numerous tables have been devised to assist designers in combating serious galvanic corrosion between dissimilar metals. These tables usually list the different metals from anodic to cathodic. Metals that are close together in the relative series have a low potential difference while those at the opposite extremes of the series will exhibit a larger potential difference. No table is universally acceptable because the series changes under different conditions. The standard electrical potentials are of little value in establishing galvanic activity in an actual environment. The standard potential of a metal is the potential measured in equilibrium with a molar concentration of its ions. This condition is not encountered in the present invention because the galvanic system is dynamic, and the potentials of the dissimilar metals are not at equilibrium. In addition, the metals are not in solutions of identical ions, and the reaction is not controlled solely by difference of potential.

In addition to the type and concentration of the conductive medium, many other factors affect the kinetics and severity relationships of metals in a particular series. Some of these factors include: Surface roughness, surface finish, area ratio of anode to cathode, heat treatment, motion or aeration of the electrolyte, temperature, and pH. In particular the pH of an electrolyte can cause a reversal of some metals in a series, causing what would be the less active cathodic metal to corrode instead of the active anodic metal. Basic factors are the electrical potentials of the electrodes, current, and resistances expressed by:

$$E_c - E_a = IR_e + IR_m$$

where:

$E_c$=potential of the cathode (as polarized), $E_a$ = potential of the anode (as polarized),
$R_e$ = resistance of the electrolyte solution path,
$R_m$ = resistance of the electrodes.

The electrical activity of the anode is proportional to the area of the cathode. If the cathode area is two to three times the area of the anode, and if the polarization is negligible, the current is generally increased by the same factor. The same relationship prevails if the anode is decreased relative to the cathode, in effect increasing the area of the anode which reduces galvanic current density and makes normal cell corrosion dominant.

SUMMARY, RAMIFICATIONS, AND SCOPE

Accordingly, the reader will see that the galvanic-powered wetness sensor feature of this invention can be used in many applications where sensing and monitoring of wetness is important. For example: a double-walled boat hull may have this sensor embedded between the walls. This feature would allow a signal to be provided if water breached the outer hull. The use of the self-powered feature of this invention is important in such applications.

Although the description above contains many specifications, these should not be construed as limiting the scope of the invention but as merely providing an illustration of the presently preferred embodiment of this invention. For example, many other materials besides chrome pickled AZ 31B magnesium and passivated AM 350 grade stainless steel will produce a galvanic reaction in an electrolyte; the serpentine arrangement of the sensor may be straightened or further convoluted; the preferred arrangement of the anode located coaxial within the cathode can be changed to parallel anode and cathode, multiple anodic and cathodic elements, and these can be wired in series or in parallel depending on the voltage and current desired.

Thus, the scope of the invention should be determined by the appended claims and their legal equivalents, rather than by the examples given.

I claim:

1. A body waste detecting device, comprising:
   an elongated flexible sensor comprising a flexible conductor energized by electrogalvanic action to produce a signal in response to contact with body waste, said flexible sensor comprises an axial conductor, a coaxial conductor positioned coaxial with and substantially surrounding said axial conductor and a dielectric located between said axial conductor and said coaxial conductor; and
   an electrical circuit responsive to said signal to produce an alarm;
   wherein said axial conductor comprises a first metal and said coaxial conductor comprises a second metal different than the first metal such that when said dielectric absorbs said body waste an electrical current flows between said axial conductor and said coaxial conductor.

2. The body waste detecting device of claim 1, wherein said elongated flexible sensor further comprises an adhesive strip.

3. The body waste detecting device of claim 1, comprising a casing that includes said electrical circuit.

4. A device according to claim 3 in which said casing is hermetically sealed.

5. The body waste detecting device of claim 1, wherein said flexible conductor comprises a material that is degradable by the effect of urine.

6. A device according to claim 5 in which said elongated flexible sensor is disposable.

7. The body waste detecting device of claim 1, wherein said axial conductor is anodic in relationship to said coaxial conductor.

8. The body waste detecting device of claim 7, wherein said coaxial conductor has a surface area greater than the surface area of said axial conductor.

9. The body waste detecting device of claim 8, wherein said coaxial conductor comprises a braided wire separated from said axial conductor by said dielectric.

10. The body waste detecting device of claim 9, wherein said dielectric comprises a strongly absorbent and hydrophilic material.

11. The body waste detecting device of claim 1, wherein said electrical circuit generates a voltage potential in response to said electrogalvanic action.

12. The body waste detecting device of claim 11, further comprising:
    electrical connecting means connecting said elongated flexible sensor to said circuit; and
    an alarm unit responsive to said voltage potential.

13. A device according to claim 12 in which said alarm unit comprises a visual alarm.

14. A device according to claim 12 in which said alarm unit comprises an audible alarm.

15. A device according to claim 12 in which said alarm unit comprises a transmitter to allow remote sensing and alarm notification.

16. The body waste detecting device of claim 15 wherein the transmitter comprises a frequency modulated transmitter for use in the frequency range of about 91 to about 97 megahertz, the frequency modulated transmitter comprising an electret condenser microphone responsive to voltage generated by said electrical current, a first transistor having an oscillating frequency which varies in proportion to a signal provided by the electret condenser microphone, a second transistor which amplifies a signal from the first transistor, an antenna which receives and radiates a signal from the second transistor and a tuning coil for controlling a frequency of the radiated signal.

* * * * *